(12) United States Patent
Zimmermann et al.

(10) Patent No.: US 8,584,510 B2
(45) Date of Patent: Nov. 19, 2013

(54) METHOD AND DEVICE FOR DETERMINING A PRESSURE PARAMETER OF A PLANT SAMPLE

(75) Inventors: Dirk Zimmermann, Zug (CH); Ernst Bamberg, Kelkheim Taunus (DE); Ulrich Zimmermann, Walbrunn (DE); Markus Westhoff, Wuerzburg (DE); Randolph Reuss, Heidelberg (DE); Albert Gessner, Wuerzburg (DE); Willibald Bauer, Hafenlohr (DE)

(73) Assignees: Max-Planck-Gesellschaft zur Foerderung der Wissenschaften e.V., Munich (DE); Julius-Maximilians-Universitaet Wuerzburg, Wuerzburg (DE); Zim Plant Technology GmbH, Hennigsdorf (DE)

( * ) Notice: Subject to any disclaimer, the term of this patent is extended or adjusted under 35 U.S.C. 154(b) by 549 days.

(21) Appl. No.: 12/863,770

(22) PCT Filed: Jan. 21, 2008

(86) PCT No.: PCT/EP2008/000424
§ 371 (c)(1),
(2), (4) Date: Nov. 10, 2010

(87) PCT Pub. No.: WO2009/092389
PCT Pub. Date: Jul. 30, 2009

(65) Prior Publication Data
US 2011/0049264 A1    Mar. 3, 2011

(51) Int. Cl.
*G01N 33/483* (2006.01)
(52) U.S. Cl.
USPC .......................................................... 73/37

(58) Field of Classification Search
USPC .............................................. 73/862.581, 37
See application file for complete search history.

(56) References Cited

U.S. PATENT DOCUMENTS

| 4,160,374 A * | 7/1979 | Crump et al. ............ 73/76 |
| 2008/0046130 A1* | 2/2008 | Faivre et al. .......... 700/284 |

FOREIGN PATENT DOCUMENTS

WO    2005070190 A1    8/2005

OTHER PUBLICATIONS

Geitmann, "Experimental Approaches Used to Quantify Physical Parameters at Cellular and Subcellular Levels", American Journal of Botany, vol. 93, pp. 1380-1390 (2006).
McBurney, "The Relationship Between Leaf Thickness and Plant Water Potential", Journal of Experimental Botany, vol. 43, pp. 327-335 (1992).
Scholander et al., "Sap Pressure in Vascular Plants", Science, vol. 148, pp. 339-346 (1965).
Zimmermann et al., "Water ascent in tall trees: does evolution of land plants rely on a highly metastable state?", New Phytologist, vol. 162, pp. 575-615 (2004).
Zimmermann et al., "Kontinuierliche Druckmessung in Pflanzenzellen", Die Naturwissenschaften, p. 634 (1969).

* cited by examiner

*Primary Examiner* — Hezron E Williams
*Assistant Examiner* — Paul West
(74) *Attorney, Agent, or Firm* — Caesar, Rivise, Bernstein, Cohen & Pokotilow, Ltd.

(57) ABSTRACT

A method of determining a pressure parameter of a plant sample (1) comprises the steps of subjecting the plant sample (1) to a clamp pressure ($p_{clamp}$) created with a clamp device (10), measuring at least one pressure response value ($p_p$) of the plant sample (1), which depends on the clamp pressure ($P_{clamp}$)/and determining the pressure parameter on the basis of the at least one pressure response value ($p_p$), wherein the clamp pressure ($p_{clamp}$) is adjusted, such that the plant sample (1) has a viscoelastic pressure response to the clamp pressure ($p_{clamp}$). Furthermore, an apparatus (100) for determining a pressure parameter of a plant sample (1) is described.

38 Claims, 6 Drawing Sheets

METHOD AND DEVICE FOR DETERMINING A PRESSURE PARAMETER OF A PLANT SAMPLE

TECHNICAL FIELD OF THE INVENTION

The present invention relates to a method of determining a pressure parameter of a plant sample, in particular to a method of determining a water status related pressure parameter of the plant sample. Furthermore, the present invention relates to a device adapted for conducting a method of determining a pressure parameter. Preferred applications of the invention are in the field of non-invasive monitoring of the water relations of plants, in particular of intact plant leaves, the control of irrigations systems, and in basic research.

TECHNICAL BACKGROUND

Water management is an important aspect for successful agricultural plant production since water stress may a pronounced effect on the vegetative growth, and number and size and quality of fruits. Excessive irrigation is expensive, can cause vigorous vegetative growth as well as delayed ripening and increases the need for disease and pest control. Excessive water supply will also cause percolation of water below the root zone, leaching nitrate and other chemicals into groundwater. Furthermore, the need to optimize crop water use has become more important given the decrease in the amount of available water for agriculture and the increase in the irregularity of rain distribution.

In practice, various irrigation methods have been developed for optimizing the amount of water and frequency of application in dependency on the evapotranspirative demand, weather conditions and the type of soil. Efficient irrigation requires precise information on the specific water requirements of the plant species at different growth stages and under varying (micro-)climatic conditions, and on crop water consumption to meet the correct irrigation scheduling timing and amount of water, fertilizers and to limit losses through deep percolation.

The water status of leaves can be determined using a pressure chamber (P. F. Scholander et al. in "Science" vol. 148, 1965, p. 339-346). The method is simple, but massively invasive, time-consuming and unsuitable for automation. Further drawback is that the number of leaves that can be measured is rather limited and, therefore, data can be misrepresentative of the overall in-situ conditions (due to variability in height, sun exposure, microclimate conditions, canopy circumference etc.). Most importantly and frequently ignored, the readings cannot always straightforwardly be interpreted in terms of xylem pressure and/or turgor pressure.

Further techniques for investigating the water status of plants, in particular for irrigation purposes, are known in practice. As an example, humidity sensors can be used for measuring soil moisture content directly. Although such sensors can be permanently installed at representative sites in an agricultural field, particular disadvantages are given in terms of soil heterogeneity and the requirement of a close contact to the soil matrix.

The most reliable information on the water status can be obtained if the turgor pressure in the plant cells is measured directly. Various types of turgor pressure measuring devices have been described in the past. An early example is the pressure measurement in plant cells described by U. Zimmermann et al. ("Die Naturwissenschaften", 1969, vol. 56, p. 634), whereas the turgor pressure is sensed with a combination of a micro-needle and a pressure probe. Further turgor pressure measuring techniques, like e.g. ball tonometry, micro-indentation, cantilever bending measurements or aspiration measurements have been described by U. Zimmermann et al. ("New Phytologist", vol. 162, 2004, p. 575-615) and by A. Geitmann ("American Journal of Botany", vol. 93, 2006, p. 1380-1390). As another approach, the relationship between leave thickness and plant water potential has been described by T. McBurney ("Journal of Experimental Botany", vol. 43, 1992, p. 327-335).

Generally, the conventional turgor pressure measurement techniques have disadvantages in terms of limited reliability and applicability under practical conditions of agriculture. It has been found that the results obtained with the conventional techniques have a limited significance. Furthermore, the conventional techniques are not suitable for long-term outdoor applications especially because of their susceptibility to gusty or high winds.

OBJECTIVE OF THE INVENTION

The objective of the invention is to provide an improved method and device of determining a pressure parameter of a plant sample, which is capable of overcoming limitations of the conventional techniques. In particular, the objective of the invention is to provide a facilitated, reliable, inexpensive and field-suitable technique of online-monitoring a plant water status.

The above objectives are achieved with methods and devices comprising the features of the independent claims. Advantageous embodiments and applications of the invention are defined in the dependent claims.

SUMMARY OF THE INVENTION

According to a first aspect, the invention is based on the general technical teaching of providing a method of determining a pressure parameter of a plant sample, whereas the plant sample is subjected to a clamp pressure, at least one pressure response value of the plant sample is measured, which depends on the clamp pressure, and the pressure parameter to be obtained is determined on the basis of the at least one measured pressure response value. According to the invention, the clamp pressure is adjusted, such that the plant sample has a viscoelastic pressure response to the clamp pressure.

With other words, the clamp pressure is selected such that the plant sample has a visco-elastic behaviour. Accordingly, if the plant sample is subjected to the predetermined clamp pressure, the plant sample is compressed to a certain degree, whereas with a release of the clamp pressure, the plant sample is relaxing. Preferably, the relaxation results in a reversible formation of the pre-pressing geometry. However, a complete reversible relaxation is not strictly necessary for implementing the invention. A partial relaxation towards the pre-pressing geometry may be enough for providing a precise and reliable pressure parameter of the plant sample. If the clamp pressure would be too low, a visco-elastic pressure response would not be obtained, the clamp pressure would be absorbed by parts of the plant sample, which do not depend on the turgor-pressure. On the other hand, if the clamp pressure would be too high, the plant sample could be damaged.

The inventive adjustment of the clamp pressure represents an essential advantage compared with the conventional techniques as the at least one measured pressure response value yields precise information on the water status of the plant and allows an access to the turgor pressure of the plant cells of the investigated plant sample. With the inventive adjustment of the clamp pressure, the reliability and reproducibility of the determined pressure parameter is essentially improved. Accordingly, measurements under practical conditions of agriculture can be facilitated, whereas the inventive apparatus can be handled with a reduced risk of an operating error.

According to a second aspect, the invention is based on the general technical teaching of providing an apparatus for determining a pressure parameter of a plant sample, in particular with a method according to the above first aspect, comprising a clamp device (or: clamp pressure generating device) adapted for subjecting the plant sample to a clamp pressure, a sensor device (or: pressure response sensing device) adapted for sensing at least one pressure response value of the plant sample, whereas the at least one pressure response value depends on the clamp pressure, and an adjusting device, which is adapted for adjusting the clamp pressure, such that the plant sample has an viscoelastic pressure response to the clamp pressure.

According to a third aspect, the invention is based on the general technical teaching of providing an irrigation installation including at least one pressure parameter determining apparatus according to the above second aspect and at least one irrigation device, which is adapted to be controlled in dependence on the pressure parameter determined with the pressure parameter determining apparatus. Advantageously, a plurality of pressure parameter determining apparatuses can provide a network, which is connected with one or multiple irrigation devices. Furthermore, the function of the irrigation installation can be advantageously improved if it is provided with at least one further monitoring component including a camera device and/or weather (e.g. temperature, relative humidity, light intensity, rain precipitation) monitoring station.

According to preferred embodiment of the invention, the clamp pressure adjustment comprises a clamp device calibration, whereas the plant sample is subjected to multiple test clamp pressure pulses (varying in duration and/or amplitude) and relaxation responses of the plant sample are measured, which are associated to each of the test clamp pressure pulses. If the relaxation response results in an at least partially (preferably complete) reversible relaxation of the plant sample, the associated test clamp pressure is selected as the clamp pressure to be used for the further measurements. This calibration procedure has a particular advantage in terms of optimizing the clamp pressure for a particular plant sample under investigation. Furthermore, the calibration procedure can be used for collecting reference plant data.

Alternatively, the inventive clamp pressure adjustment can be conducted on the basis of predetermined reference plant data.

As an example, reference plant data can be collected in data storages or data tables, whereas the optimum clamp pressure is listed in dependency on the plant species and further detailed physiological properties of the plant sample (e.g. age, state of growth, fructification, metabolism) and soil properties. The reference data can be obtained by measurements, e.g. by the above calibration procedure. With the use of the predetermined reference plant data, a repeated calibration can be avoided so that the measurement is further facilitated.

The plant sample to be investigated generally comprises any part of a biological plant, in particular a plant leaf or another plant organ. The invention has been tested in particular with the intact plants grapevine, liana, banana tobacco, eucalyptus, maple, avocado and fruit trees.

The pressure response value generally comprises any type of a physical measure being characteristic for the direct or delayed response of the plant sample to an external pressure.

It is a particular advantage of the invention that various types of pressure response values can be measured and further evaluated for determining the pressure parameter. According to a first variant, an attenuated clamp pressure (output pressure) of the plant sample can be measured as the pressure response value. The attenuated clamp pressure is the pressure value, which can be sensed on a first side of the plant sample, while the clamp pressure is exerted to the opposite second side of the plant sample. As an example, if the plant sample comprises a plant leaf, the clamp pressure is subjected to the upper side of the leaf and the attenuated clamp pressure is measured at the opposite, lower side of the leaf. As the clamp pressure is partially absorbed by the plant sample, an attenuation occurs so that the attenuated clamp pressure is lower than the clamp pressure.

According to a second variant, an output force of the plant sample is measured, which output force is created in response to the exertion of the clamp pressure. The output force can be measured with a force sensor, which is arranged on a side of the plant sample in opposite relationship to the side of clamp pressure exertion. Measuring the output force of the plant sample in response to the clamp pressure represents an advantage as the output force is measured without a dependency on an eventual pronounced deformation of the plant sample.

According to a third variant, measuring of the at least one pressure response value comprises measuring at least one electrical conductivity value of the plant sample. Advantageously, this embodiment of the invention uses the fact that the pressure and the electrical membrane potential of plant cells are coupled with each other. With a varying turgor pressure, the membrane potential is varied, which can be sensed with an electrode device. Furthermore, plants have a surface potential and a surface conductivity. With the application of at least two sensor devices arranged within a mutual distance on the plant sample, pressure gradients along the plant sample can be sensed.

Another advantage of the invention is given by the different pressure parameters, which can be determined as characteristics of the water status of the plant. Firstly, the at least one measured pressure response value can be directly provided as the pressure parameter to be determined. The water status can be derived directly from the measured pressure response value e.g. by the measured attenuated clamp pressure, output force or electrical conductivity. Alternatively, a plurality of pressure response values can be measured, whereas the pressure parameter to be obtained is given by a quantitative changing measure of the pressure response values. To this end, an evaluating device is provided, which is adapted for determining the quantitative changing measure of the pressure response values. According to a further alternative, the pressure parameter comprises the cell turgor-pressure of the plant sample, which can be calculated on the basis of the at least one measured pressure response value. Advantageously, the turgor pressure represents a direct characteristic of the water status of the plant. With calculating the turgor-pressure, the maximum reproducibility and comparability of the measurement results are obtained.

Preferably, the cell turgor pressure is determined on the basis of at least one transfer function value which depends on the clamp pressure and the measured attenuated clamp pressure. Generally, the transfer function is a characteristic parameter, which depends on turgor pressure. The transfer function can be constructed in dependency on the particular application of the invention, e.g. with a simulation function or predetermined reference data. However, preferably, the transfer function is given by the quotient of the attenuated clamp pressure and the clamp pressure. In this case, the calculation of the turgor pressure is facilitated.

According to further embodiments of the invention, the determination of the quantitative changing measure comprises a calculation of a difference quotient of subsequent pressure response values, a first derivative of the pressure response values, a second derivative of the pressure response values, a fluctuation rate of the pressure response values, and/or a variation pattern of the pressure response values. The determination of the quantitative changing measure has the particular advantage that individual, plant sample-specific influences on the measured pressure response value are reduced or even completely suppressed. The quantitative changing measure can be determined with respect to time or a varying measurement condition. Preferably, at least one physical or chemical environmental condition of the plant sample, in particular at least one of illumination intensity, temperature, relative humidity, wind speed, and/or at least one physiological condition of the plant sample, in particular at least one of transpiration, stomata activity, photosynthesis and an active substance concentration, e.g. a hormone, pesticide and/or herbicide concentration can be varied.

A further advantageous embodiment of the invention is characterized by the step of selecting a measurement location on the plant sample. The measurement location can be selected with respect to a distance between the measurement location and an edge of the plant sample and/or a structural element, e.g. a plant vessel or any protruding part on the plant sample surface. Advantageously, selecting the measurement location allows a further optimization of the pressure parameter determination. With the simultaneous measurement at a plurality of plant samples, selecting identical measurement locations, e.g. on plant leaves, improves the compatibility of the measurement results.

According to the invention, the step of adjusting the clamp pressure can be further modified as follows. Firstly, a certain clamping pad can be selected in dependency on the type of the plant sample. As examples, a pair of planar clamping pads can be selected for measurements at planar plant samples, e.g. plant leaves. Alternatively, curved, surface-structured and surface structure-adaptable clamping pads can be used for measuring with plant samples having another geometry. Secondly, a clamp arm length of the clamp device can be varied for an adaptation to the type, in particular size of the plant sample and/or the clamp pressure to be exerted.

According to further embodiments of the invention, the pressure parameter determination can be combined with further steps comprising measuring, monitoring and/or injecting procedures. As examples at least one of illumination intensity, temperature, relative humidity, wind speed, transpiration condition, and photosynthesis condition can be measured, the plant sample can be monitored with a camera device, and/or an active substance, e.g. a hormone, pesticide and/or herbicide can be injected into the plant sample. Advantageously, a variation of the pressure parameter or the cell turgor pressure in response to an injection of the active substance can be sensed. As a further variant, a gradient of the pressure parameter or in particular a gradient of the cell turgor pressure can be measured along a plant sample surface.

According to a particular preferred embodiment of the invention, the inventive pressure parameter or in particular the cell turgor pressure is compared with at least one reference value, and a control signal is generated depending on a result of this comparison. Preferably, this embodiment of the invention provides the control signal as a result of the comparison of the pressure parameter (or the turgor pressure) with a predetermined threshold value being characteristic for the water status of the plant. As an example, if the turgor pressure decreases below a predetermined limit, the control signal can be used for operating an irrigation device. The comparing step can be implemented by the apparatus for determining the pressure parameter, by a separate operation installation, by a central control device or by the irrigation device.

Accordingly, the inventive method may comprise a step of sending the measured pressure response value, the pressure parameter, the turgor-pressure and/or the above control signal to the component, which is arranged for implementing the comparing step. Advantageously, these data can be sent via a network to a distant location, where the comparing step is implemented and a further processing of the control signal is completed.

Preferably, the irrigation device is directly controlled by at least one of the above data (measured pressure response value, pressure parameter, turgor-pressure and/or control signal). An automatic control can be implemented with a control loop comprising the apparatus for determining the pressure parameter, a comparing circuit for implementing the above comparing step and the irrigation device.

According to a further embodiment of the invention, the steps of subjecting the plant sample to the clamp pressure and measuring the pressure response values of the plant sample can be conducted on different sides of the plant sample. Advantageously, this can provide more detailed information on the water status of the plant sample.

According to a further embodiment of the invention, energy is supplied to the pressure parameter determining apparatus (including the equipment for data storage und data transfer) using an energy supply device connected with the clamp device and/or the sensor device, preferably a solar cell or a fuel cell device in combination with an energy accumulator, like a rechargeable battery. Advantageously, the energy supply device can be controlled such that electrical energy is supplied to the pressure parameter determining apparatus (including the equipment for data storage und data transfer) in dependency on the time of day. As an example, at noon the electrical energy supply can be increased when the irrigation system requires frequent measurements, while the electrical energy supply can be reduced down to zero in the evening or at night.

Further independent subjects of the invention are a computer program residing on a computer-readable medium, with a program code for carrying out at least one step of a method of determining a pressure parameter of the plant sample according the above first aspect, and an apparatus comprising a computer-readable storage medium containing program instructions for carrying out at least one step the method of determining a pressure parameter of the plant sample.

As a further modification, it is possible to use the invention for determining a pressure parameter of other biological or non-biological material, like e.g. a work-piece or a consumer good. For example, the following non-biological samples can be investigated with the inventive method (e.g. cellular material, cork, synthetic materials, polymers, hydro gels).

BRIEF DESCRIPTION OF THE DRAWINGS

Further details and advantages of the invention are described in the following with reference to the attached drawings, which show in.

EMBODIMENTS OF THE INVENTION

Preferred embodiments of the invention are described in the following with exemplary reference to measurements with plant leaves. It is noted that the implementation of the invention is not restricted to this type of samples, but correspondingly possible with other types of plant samples, like e.g. plant tissue or other parts of plants (e.g. needles, stem, shoots, excised leaves, fruits, roots). Furthermore, the invention can be used with living plants or in particular for research purposes with plant fragments separated from a living plant.

1. Methods of Determining a Pressure Parameter of a Leaf Sample

Figure 1:
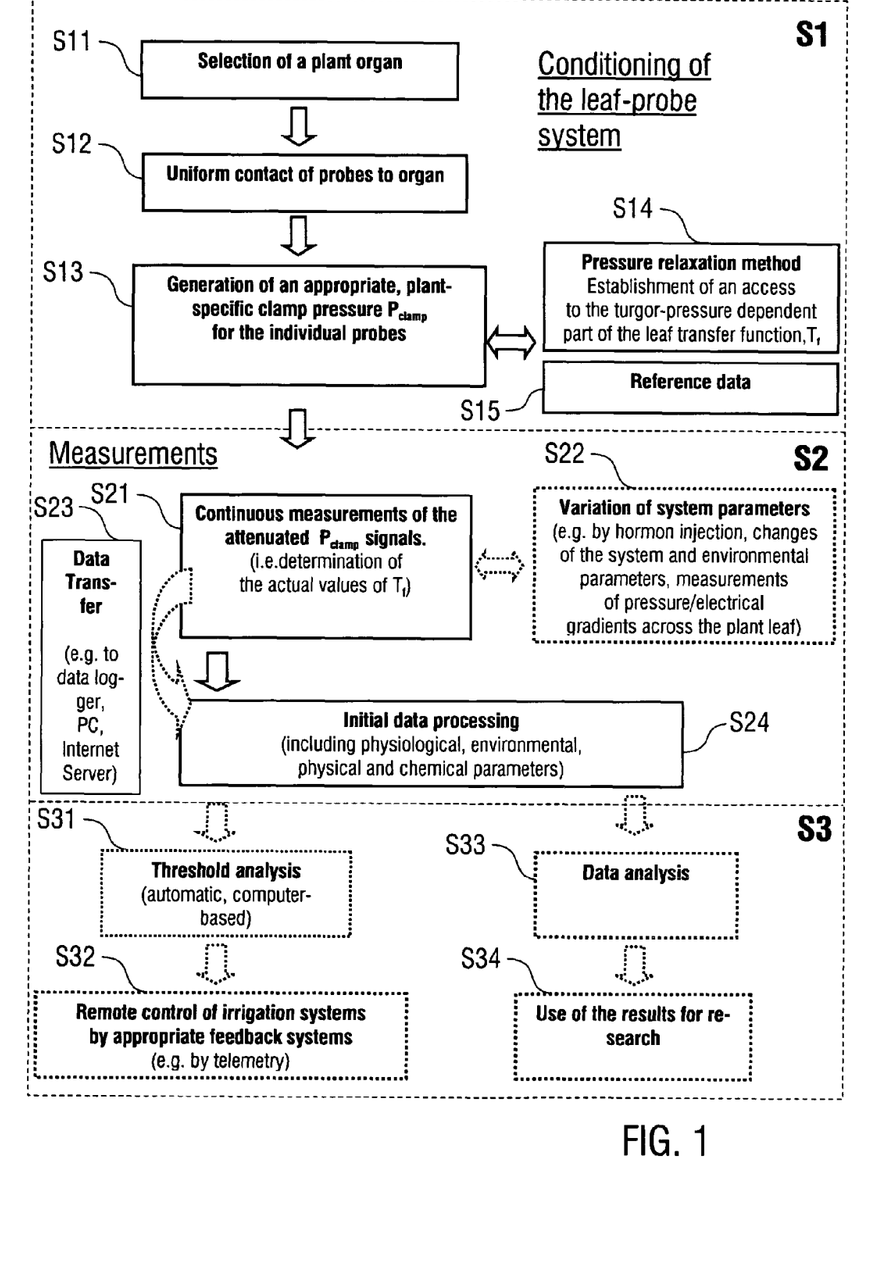
FIG. 1: a schematic flow chart illustrating features of preferred embodiments of the inventive method.

Features of preferred embodiments of the inventive method of determining a pressure parameter of a plant sample are schematically summarized in FIG. 1. Generally, the method comprises three main steps of subjecting the plant sample to a clamp pressure (step S1), measuring at least one pressure response value of the plant sample (step S2) and data analysis with a determination of the pressure parameter to be investigated (step S3).

While details of steps S1 to S3 are described in the following, further reference is made to FIG. 2 which schematically illustrates an embodiment of an apparatus 100 for determining a pressure parameter of a plant leaf 1 with the methods according to FIG. 1. Apparatus 100 comprises a clamp device 10 with first and second clamp pads 11, 12, clamp arms 13 and a force element 14, a sensor device 20, an adjusting device 30 and an evaluating device 40. The sensor device 20 is integrated into the second clamp pad 12. With the clamp device 10, the plant leaf 1 is subjected to a clamp pressure between the clamp pads 11 and 12. Further details of the apparatus 100 are described below.

Step S1 includes the conditioning of the leaf-sensor-system with a selection of a plant organ to be investigated (step 11), a provision of a uniform contact of clamp pads 11, 12 of the clamp device 10 with the selected organ (step S12) and a generation of the clamp pressure (step S13). According to the essential feature of the present invention, the clamp pressure is selected with a pressure relaxation method (step S14) and/or with an access to reference data (step S15) such that the plant leaf has a visco-elastic pressure response.

The plant organ selection step S11 includes the selection of a certain leaf 1 of a plant in an agricultural plant field or under laboratory conditions, a selection of a measurement location, where the clamp device 10 and a pressure response value sensing device 20 are positioned and/or a selection of a certain distance of the measurement location with respect to the edge of a plant leaf 1. These selections are made in dependency on the particular application of the invention. For measuring very sensitively water loss the clamp is preferentially located close to the periphery of the leaf, for measuring the water supply from the roots to the leaves, the clamp is preferentially positioned close to the main vein of the leaf.

With step S12, the uniform contact of the clamp pad with the plant leaf is provided. To this end, step S12 may include a step of a selection of an appropriate pad shape, e.g. a pair of pads with planar or curved surfaces. Alternatively or additionally, pads with a structured surface having a complementary geometry with regard to the surface of the plant leaf can be selected.

The appropriate, plant specific clamp pressure is applied to the plant leaf on the basis of an adjustment with the adjusting device 30. If the clamp pressure is selected with the pressure relaxation method (calibration), step S14 includes the steps of subjecting the plant leaf to test clamp pressure pulses. A series of test clamp pressure pulses with increasing clamp pressure amplitude (and duration) are applied to the plant leaf. After each test clamp pressure pulse, the clamp pressure is released for monitoring the relaxation behaviour of the plant leaf. If the plant leaf shows a reversible relaxation, i.e. if the pressure returns to the previous value in a very short time (e.g. up to 60 seconds), this pressure value is used as a appropriate clamp pressure to be applied with step S13.

The measurement step S2 includes continuous measurements of output pressures (attenuated clamp pressures) with the sensor device 20 (step S21). As an example, pressure values are recorded every 5 s if short-term experiments (e.g. for up to 1 day) are performed. For long-term measurements it is enough if every 15 min a value is recorded. The recording frequency depends on the electric energy which is available. Under field conditions usually solar energy is used for charging batteries. Alternatively, a fuel cell can be used as an energy supply. Optionally, certain system parameters can be varied during the measurement of the attenuated clamp pressures (step S22). The variation step S22 includes e.g. the variation of physical or chemical environment parameters or the injection of active substances, like e.g. hormones or pesticides or herbicides. Simultaneously, pressure gradients or gradients of electrical conductivity across the plant leaf can be measured.

The measured attenuated pressure signals are transferred to a data logger, a computer or a server in a network (step S23) either by cable or by wireless transmitter-receiver-system. The data transfer S23 is conducted e.g. to the internet. The transferred data are subjected to data processing for determining at least one pressure parameter on the basis of the measured pressure response values (step S24). The pressure parameter to be determined comprises at least one of the measured pressure response value(s), a cell turgor pressure ($p_c$) and a quantitative changing measure of the pressure response values.

The further analysis (step S3) may comprise a threshold analysis (step S31) for generating a control signal for an irrigation system and/or a further data analysis (S33) for the purpose of further research (step S34). On the basis of the control signal generated with step 31, irrigation systems are controlled. Feedback systems, e.g. control loops are provided for controlling the irrigation of even the plant or field of plants at which the pressure measurement has been conducted (step S32).

2. Theory of Pressure Response and Turgor-Pressure Parameter Determination

Figure 3:
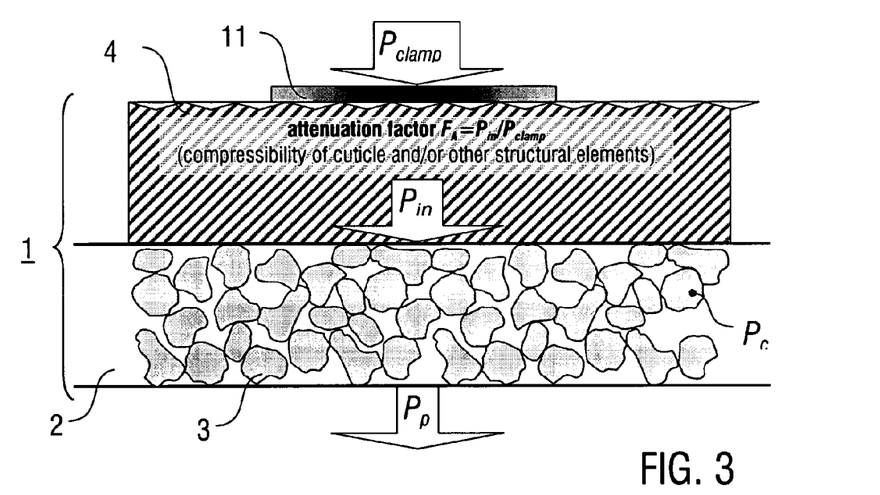
FIG. 3: a schematic model representation of a plant sample used for illustrating the theoretical background of the inventive method.

The generation and measurement of a pressure response of a plant sample and the analysis thereof is described with reference to FIG. 3, which shows an enlarged sectional schematic view of a plant leaf 1. Plant leaf 1 comprises the plant tissue 2 with turgescent cells 3 and the cuticle (including other structural elements) 4.

The input pressure seen by the cells 3 in the leaf 1, $P_{in}$, is only equal to the external clamp pressure, $P_{clamp}$, if the pressure signal is transferred lossless to the cells 3. However, losses usually occur due to the compressibility and the deformability of the silicone of the sensor device 20 (see below) as well as of the compressibility of the cuticle 4 and other structural elements of the leaf 1. Therefore, only a fraction of $P_{clamp}$ is seen by the cells 3, i.e. the attenuation factor, $F_a=P_{in}/P_{clamp}$, is smaller than unity. In the case of the rigid leaves of e.g. vine leaves $F_a$ is c. 0.3 as evidenced by control experiments of the inventors. $F_a$ can be assumed to be constant because $P_{clamp}$ is kept constant during the measurement period.

Thus the output pressure (or: attenuated clamp pressure), $P_p$, is only determined by a cell transfer function, $T_f(V)$, where V is the patch leaf volume. $T_f(V)$ determines the fraction of $P_{in}$ that is sensed by the sensor device 20 (i.e. $P_p$). $T_f$ is dimensionless and assumes values between zero and unity:

$$P_p = T_f(V) \cdot P_{in} \tag{1}$$

The apparatus 100 measures the attenuated clamp pressure, $P_p$, of the leaf 1 in response to the external clamp pressure, $P_{clamp}$. The attenuation of $P_{clamp}$ depends on the leaf transfer function. The magnitude of the leaf transfer function, and thus attenuation of external pressure signals, is determined by a plant-specific, turgor pressure-independent term (related with the compression of the cuticle, cell walls and other structural elements) and a turgor pressure-dependent term, $T_f$. With the inventive adjustment of the clamp pressure, the turgor pressure—independent term is eliminated. The following equations show that $T_f$ is a power function of $P_c$ and that $T_f$ assumes values close to zero if $P_c$ is high and vice versa values close to unity if $P_c$ is low.

The function of $T_f$ on leaf volume, V, is given at constant ambient temperature, T, by Eq. 2:

$$T_f = -\left(\frac{\delta T_f}{\delta V}\right)_T \cdot V \tag{2}$$

The relative volume change $\delta V/V$ of the leaf patch is correlated to the turgor pressure change, $\delta P_c$, by the average volumetric elastic modulus, $\epsilon_p$, of the tissue beneath the clamp.

$$\left(\frac{\delta P_c}{\delta V}\right)_T = \frac{\epsilon_p}{V} \tag{3}$$

$\epsilon_p$ is a complex parameter and will depend inter alia on the magnitude of the turgor pressure $P_c$. For an approximation it can be assumed that $\epsilon_p$ increases linearly with $P_c$:

$$\epsilon_p = aP_c + b \tag{4}$$

where a and b are constants. Because of the viscoelastic properties of the cell walls the magnitude of the constants depends on the duration of pressure application. The constants are relatively large if rapid turgor pressure changes are induced (e.g. by using the clamp device 10), whereas slow turgor pressure changes (e.g. induced by transpiration) result in small values.

Combining Eqs. 2-4 leads to Eq. 5:

$$\frac{dT_f}{T_f} = -\frac{dP_c}{aP_c + b} \tag{5}$$

Eq. 5 can be integrated if it is assumed for a first approximation that at $P_c=0$ $T_f=1$ and that the internal osmotic pressure of the cells 3 remains nearly constant in the range of cell turgescence. After appropriate re-arrangements Eq. 6 is obtained:

$$T_f = \left(\frac{b}{aP_c + b}\right)^{\frac{1}{a}} \tag{6}$$

and, respectively, if the denominator is replaced by Eq. 4:

$$T_f = \left(\frac{b}{\epsilon_p}\right)^{\frac{1}{a}} \tag{7}$$

Introducing of Eq. 6 into Eq. 1 yields a relationship between the parameters $P_p$ and $P_{in}$:

$$P_p = \left(\frac{b}{aP_c + b}\right)^{\frac{1}{a}} P_{in} \tag{8}$$

Eq. 8 can experimentally be proved. Inspection of the equation shows that the attenuated clamp pressure, is a power function of the turgor pressure $P_c$. The exponent of the function is equal or smaller than unity. If a=1 and b<<$P_c$, Eq. 8 goes over into $P_p = b \cdot 1/P_c$, i.e. both parameters are directly reciprocally coupled with each other. Thus, $T_f$ assumes low values if $P_c$ is high and vice versa a value close to unity if $P_c$ is close to zero. Using appropriate values for a and b (see below) it can be shown that below $P_c$=100 kPa, $P_p$ must increase dramatically. This is of great interest for irrigation scheduling because the rapid increase of $P_p$ upon approaching the plasmolytic point allows detection of turgor pressure loss in due time.

For practical applications, following values of a and b can be assumed: a=2-10 kPa, b=2-15 kPa.

Accordingly, the turgor pressure $P_c$ can be determined as the pressure parameter on the basis of the at least one pressure response value ($P_p$).

3. Apparatus for Determining a Pressure Parameter of a Leaf Sample

Figure 2:
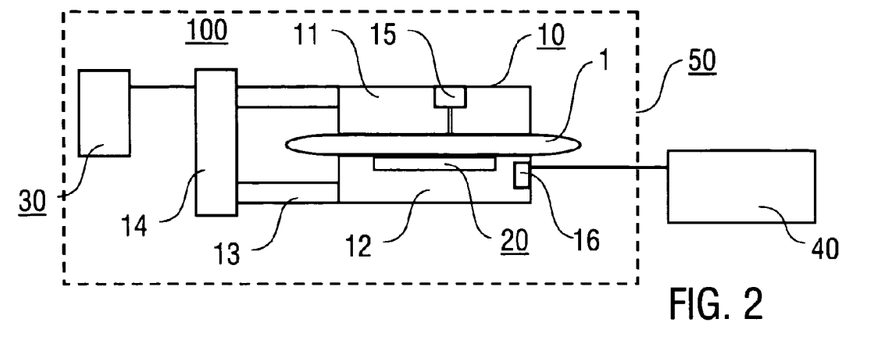
FIG. 2: a schematic illustration of a preferred embodiment of a pressure parameter determining apparatus according to the invention.
Figure 4:
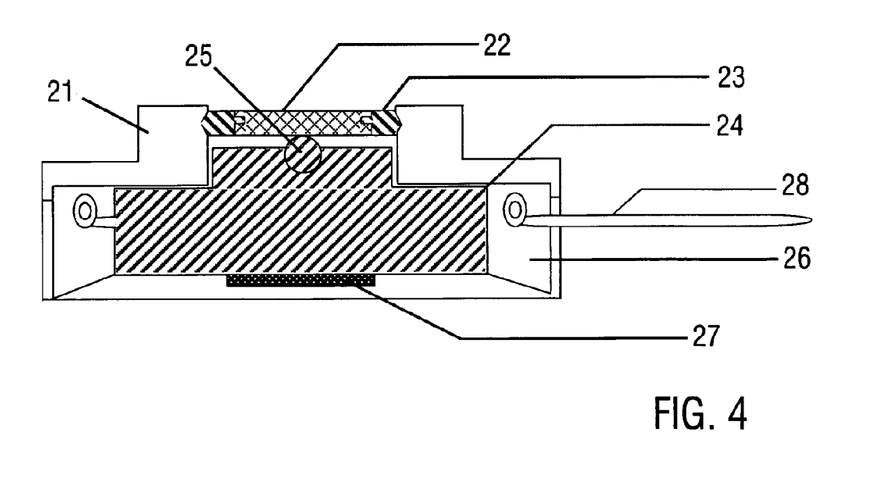
FIG. 4: a cross-sectional illustration of a pressure response value sensing device used according to the invention.

Further details of the clamp device 10, the sensor device 20, the adjusting device 30 and the evaluating device 40 are described in the following (FIGS. 2, 4).

With reference to FIG. 2, the clamp device 10 comprises two planar circular clamp pads 11, 12, where one of the clamp pads 11, 12 contains a receptacle for the integration of the sensor device 20. For pressure measurements, a leaf is positioned in the space between two clamp pads 11, 12. The clamp pads can be integrated into various types of clamp assemblies (FIGS. 5, 6).

Figure 5:
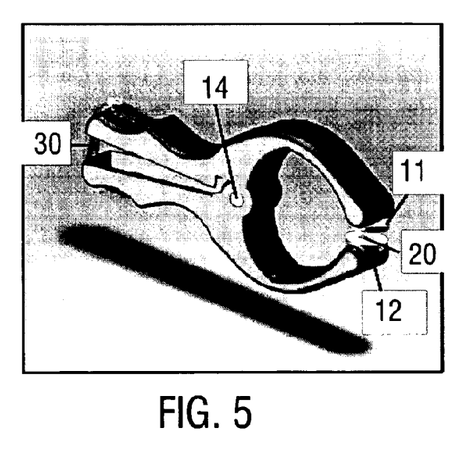
FIGS. 5 and 6: illustrations of clamp devices used according to the invention.
Figure 6:
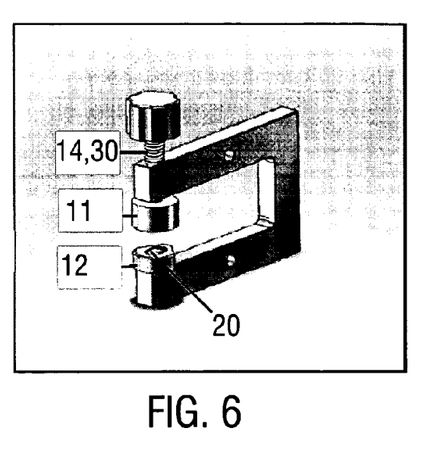

The force element 14 of the clamp device 10 is adapted for generating a clamp force, which is transmitted directly to the clamp pads 11, 12 (FIG. 6; screw clamp device) or via the clamp arms 13 (FIG. 5; spring clamp device). According to the invention, various types of clamp forces can be generated with the force element 14, e.g. an elastic spring force (see spring clamp device of FIG. 5), a static force (see screw clamp device of FIG. 6), an acoustic force, a magnetic force or an electrical force.

The sensor device 20 is integrated into the second clamp pad 12. FIG. 4 illustrates details of a preferred embodiment of a sensor device 20. This embodiment is adapted for sensing an output force transmitted by the plant leaf 1 in response to the external clamp pressure.

The sensor device 20 comprises an outer casing 21, which contains a contact disc 22, a silicone gasket 23, a force sensor 24, a silicone grouting 26, a PTFE membrane 27 and connecting cables 28. The casing 21 is integrated into the lower clamp pad 12 of the clamp device 10 (FIG. 2). Alternatively, the casing 21 can provide the clamp pad 12 as such.

The contact disc 22 comprises a plate made of a solid material, e.g. a metallic plate. The contact disc 22 is exposed to the plant leaf 1. A difference in height is provided between the upper surface of the casing 21 and the surface of the contact disc 22 (as shown in FIG. 4). This distance can be selected in the range of 10 μm to 5 mm. Alternatively, the surface of the contact disc 22 can be aligned with the upper surface of the casing 21. The silicone gasket 23 is used for positioning the contact disc 22 in the casing 21 in a movable manner and prevents ingress of moisture. Accordingly, the contact disc 22 is positioned in a floating manner on the contact sphere 25 of the force sensor 24. The contact sphere 25 provides a dot-shaped contact of the contact disc 22 with the force sensor 24. The force sensor 24 includes a piezoelectric element, which is included in a Wheatstone bridge at is known from conventional pressure sensors. The output signal of the Wheatstone bridge is transferred via the connecting cable 28 to the evaluating device 40 (FIG. 2). The sensor device 20 can be calibrated by pressurisation in a pressure chamber equipped with an integrated manometer or by loading of the contact disc with defined weights.

Alternatively, the sensor device can be provided for a force measurement with at least one cantilever sensor as it is known from scanning force microscopy.

As a further alternative, the sensor device can be adapted for measuring an output pressure or the transfer function of the leaf 1. It is based on an electronic chip strain gauge coated with a thin silicone membrane. Upon pressure application piezoresistive effects are generated that are proportional to the strains experienced by the sensor. The changes in resistance are sensed by a Wheatstone bridge integrated into the chip.

According to the invention, the sensor device can be adapted for measuring electrical conductivity of the leaf (perpendicular to the planar extension of the leaf).

According to further alternatives, the sensor device 20 can include multiple pressure or force sensors. Accordingly, multiple pressure response values can be collected simultaneously, in particular for reference purposes or for monitoring pressure gradients. In the case of a malfunction of one sensor, the remaining sensors can be used for the measurement.

If electrodes are provides in both opposing clamp pads 11, 12, the following measuring procedure can be conducted. Voltage/current pulse are supplied to the electrodes for multiple measurements of the electrical conductivity. The frequency of the pulse can be selected in the range of e.g. 0.01 Hz to 100 MHz. The pressure response can be correlated with the electrical conductivity.

Clamp devices 10 can be provided with the following further modifications. The area of the clamp pads 11, 12 and/or the length of the clamp arms 13 can be variable. The clamp pads 11, 12 can be exchangeable, so that the clamp device can be adapted to a particular plant, e.g. to plant needle samples.

The shape and/or structure of the clamp pads can be adjustable, thus the adaptation of the clamp pads to a particular plant can be further facilitated. Furthermore, a matching surface coating, e.g. made of synthetic material or by vapour deposition on metal surfaces can be provided on at least one of the clamp pads. The structure of the clamp pads can be selected according to the structure of the plant sample. Accordingly, the contact with the sample can be improved. It is even possible to measure the pressure response in plant leaf vessels, like leaf veins, or to detect cavitated vessels.

If at least one clamp pad is made of a transparent material, the clamped leaf surface can be illuminated during measurement. If at least one clamp pad is made of a porous material, the transpiration of the leaf can be facilitated.

Reference numeral 15 in FIG. 2 refers to a further optional component of the clamp device 10, which can comprise at least one of an integrated injection device, a light guiding device, and an electrode device. With the injection device 15, including an injection reservoir and an injection needle, an active substance can be applied to the leaf. Alternatively, an injection device can be provided remote from the clamp device, in particular with the irrigation device and/or with a device for a direct injection to a plant organ (e.g. roots, stem).

FIG. 2 schematically illustrates a protection device 50 covering the apparatus 100. The protection device 50 is adapted for protecting at least components 10 and 20 against humidity, extreme temperature and/or mechanical impact.

The clamp pressure exerted with the clamp device 10 is adjusted with the adjusting device 30 on the basis of reference data or with the pressure relaxation method of step S14 (FIG. 1).

The evaluating device 40 is adapted for data processing of pressure response values sensed with the sensor device 20. In particular, the evaluating device 40 is adapted for determining a quantitative changing measure of the pressure response values. The evaluating device 40 can be provided in combination with the clamp device 10 or preferably as a remote circuit component, e.g. in a central control device.

The evaluating device 40 is connected with the clamp device 10 or the sensor device 20 via a data port device 16, which is adapted for data transmission. Preferably, data port device 16 is configured for a connection with a telemetric system and/or a network for data transfer (e.g. Internet).

FIGS. 5 and 6 represent schematic diagrams of two types of clamp devices 10. According to FIG. 5, a spring clamp is provided with the clamp pads 11, 12 (including the sensor device 20) at the free ends of the clamp arms 13. A spring is used as a force element 14 for urging the spring arms 13 together. The clamp pressure (applied force of the force element 14) can be adjusted with the adjusting device 30, which comprises a stiff strap for a variation of the spring load.

The spring clamp of FIG. 5 comprises two curved clamp arms 13 bridged by a spring 14 in the middle (e.g. manufacturer Wolfcraft GmbH; microfix S, B3630Fz60; Kempenich, Germany). The clip is made of stiff synthetic material. Optimum adjustment of the clamp pressure, $P_{clamp}$, to leaf thickness and stiffness was accomplished by a stiff strap (adjusting device 30), which is made of synthetic material. The strap is spanned between the clamp arms 13 of the spring clip at the handhold site. The strap contains regularly punched holes like a belt allowing variation of length and thus of the spring load acting on the leaf between the two pads.

FIG. 6 illustrates a screw clamp with the clamp pads 11, 12 (including the sensor device 20). In this case, the force element 14 and the adjusting device 30 are provided by the screw. With the adjustment of the screw, the selected clamp pressure can be set.

According to alternative embodiments of the invention, acoustic, magnetic or electrical clamp devices can be used. While embodiments of these devices are not shown here, it is noted that these embodiments have similar structures, wherein the force element is correspondingly adapted for generating an acoustic, magnetic or electrical force. With an acoustic force, the clamp pressure is generated with the pressure of a sound wave exerted onto the plant sample. With magnetic or electrical forces, the clamp pads are urged together under the influence of external magnetic or electrical fields, respectively. Furthermore, combinations of the various types of clamp devices can be used.

Figure 7:
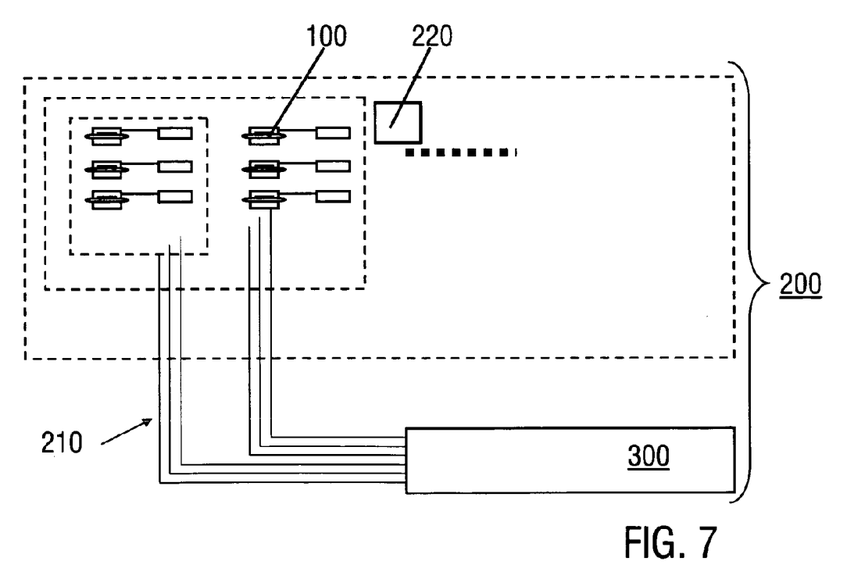
FIG. 7: a schematic illustration of an irrigation installation of the invention.

FIG. 7 schematically illustrates an embodiment of an irrigation installation 200 including a plurality of pressure parameter determining apparatuses 100 and at least one irrigation device 300, which is controlled in dependency on pressure parameters provided with the pressure parameter determining apparatuses 100. The irrigation installation 200 will be structured with groups of devices 100 arranged on leaves of a certain plant and/or groups of devices 100 distributed in a plant field (or in laboratories). This hierarchical concept can be extended to a plurality of fields in a certain landscape or even worldwide.

Reference numeral 220 in FIG. 7 refers to at least one sensor which is adapted for sensing at least one of a light intensity, temperature, relative humidity, wind speed, a transpiration condition, a photosynthesis condition and an active substance concentration, e.g. a hormone, pesticide and/or herbicide concentration. Sensor 220 is connected with the central control device and the irrigation device 300.

Data acquisition of leaf turgescence is performed by wireless transmission (telemetry) from the measuring site to a receiver station connected with a personal computer and/or with an Internet server via mobile phone. Since the data are available in real time they can be used for wireless remote control of irrigation systems. In contrast to conventional plant-based methods, the inventive method does not give only information whether or not irrigation is required, but also information how much and for how long water must be applied.

The sensor signals are acquired by telemetric systems 210 (manufacturer: Telebitcom GmbH, Teltow, Germany). The transmitters (not shown) read and amplify analog signals of the sensor device 20. Digitised data are sent together with a transmitter ID code in regular intervals via the ISM band of 433 MHz to a RF receiver unit over a distance of up to 400 m. The receiver is connected via an RS-232 interface to a personal computer or to a GPRS modem linked to an Internet server (NTBB Systemtechnik GmbH, Zeuthen, Germany) via mobile phone network. The telemetric system 210 allows simultaneous data processing of e.g. 32 sensor devices. In parallel to data acquisition by the telemetric systems data can also be stored by data loggers.

Several methods of irrigation can be used depending on the type of irrigated crop and on water availability. As an example, drip irrigation is considered as a preferable method for irrigating vineyards since the water is applied directly to the soil while the canopy remains unwetted.

4. Experimental Results

Measurements with grapevine have shown that the inventive technique is able to monitor precisely changes in turgor pressure, even at peak water demands and over the entire vegetation period. Concomitant attenuated clamp pressure and cell turgor pressure measurements (using the cell turgor pressure probe) on grapevines confirmed the predictions of the above theory. Scholander pressure chamber measurements performed in parallel to $P_p$, measurements revealed that balancing pressure values are dictated obviously by turgor pressure in the turgescent state whereas in the turgorless state they reflect the pressure needed to shift water to the excised end of the twig or leaf petiole.

Figure 8:
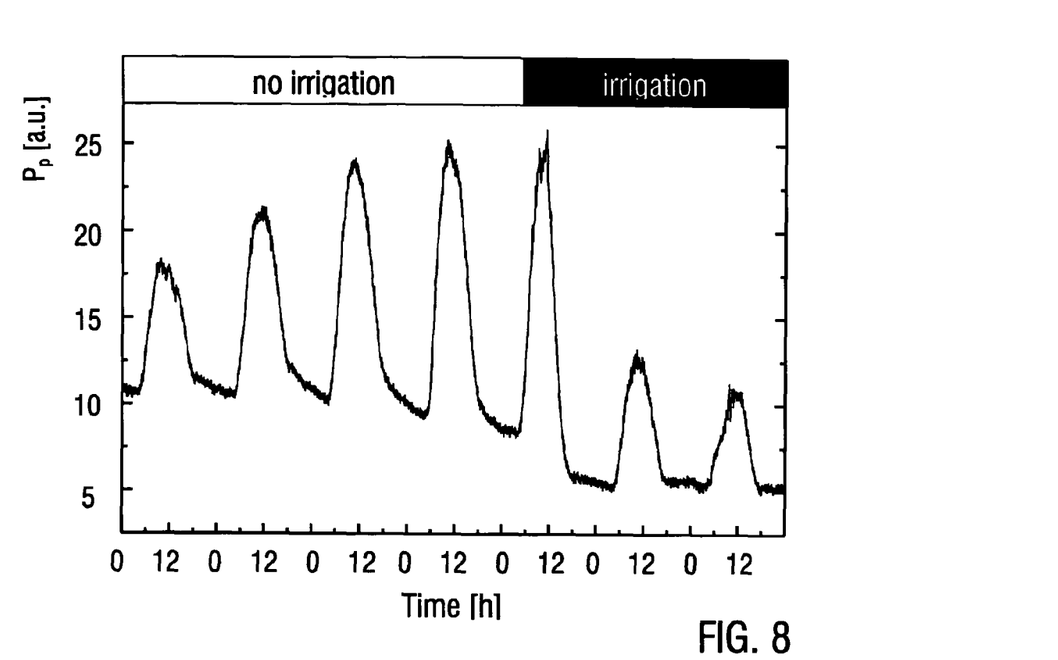
FIGS. 8 to 12: examples of experimental results obtained with the inventive technique.
Figure 9:
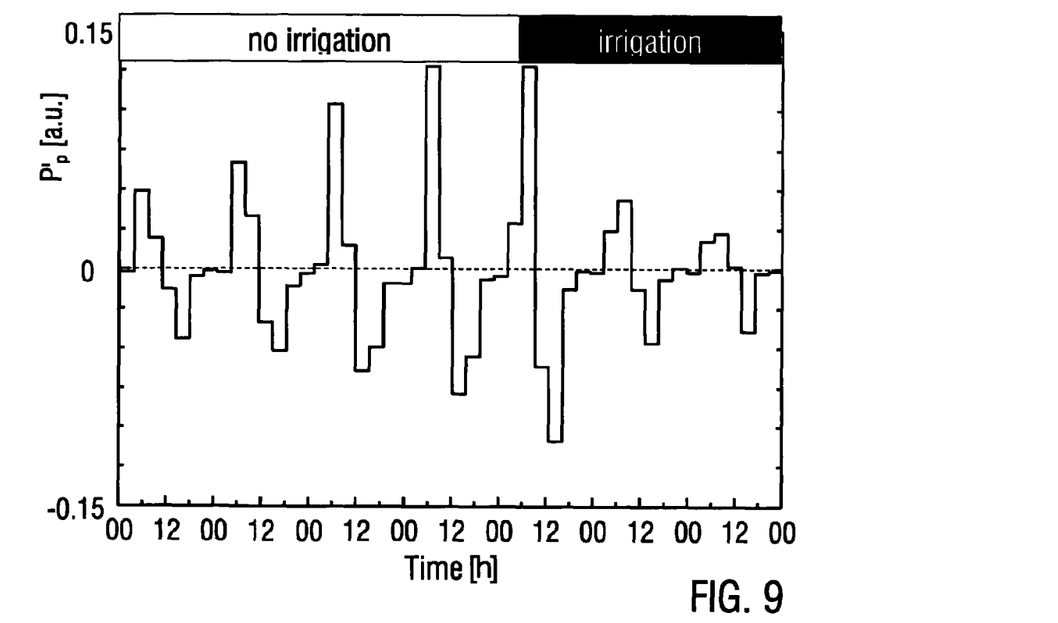
Figure 10:
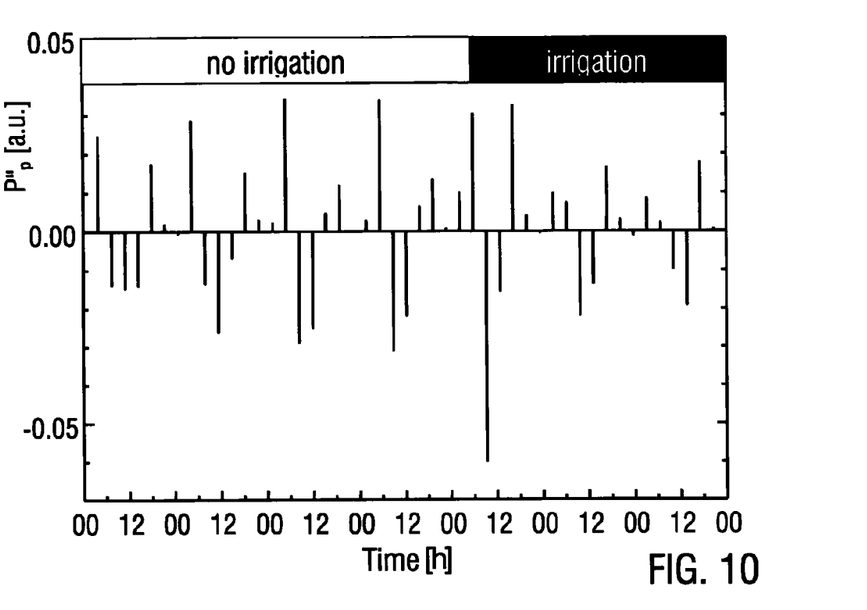
Figure 11:
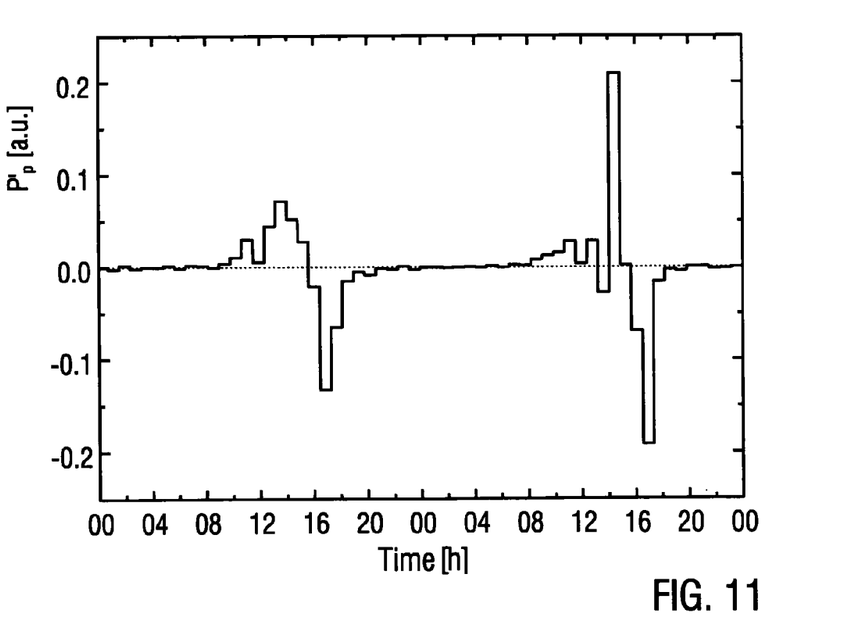
Figure 12:
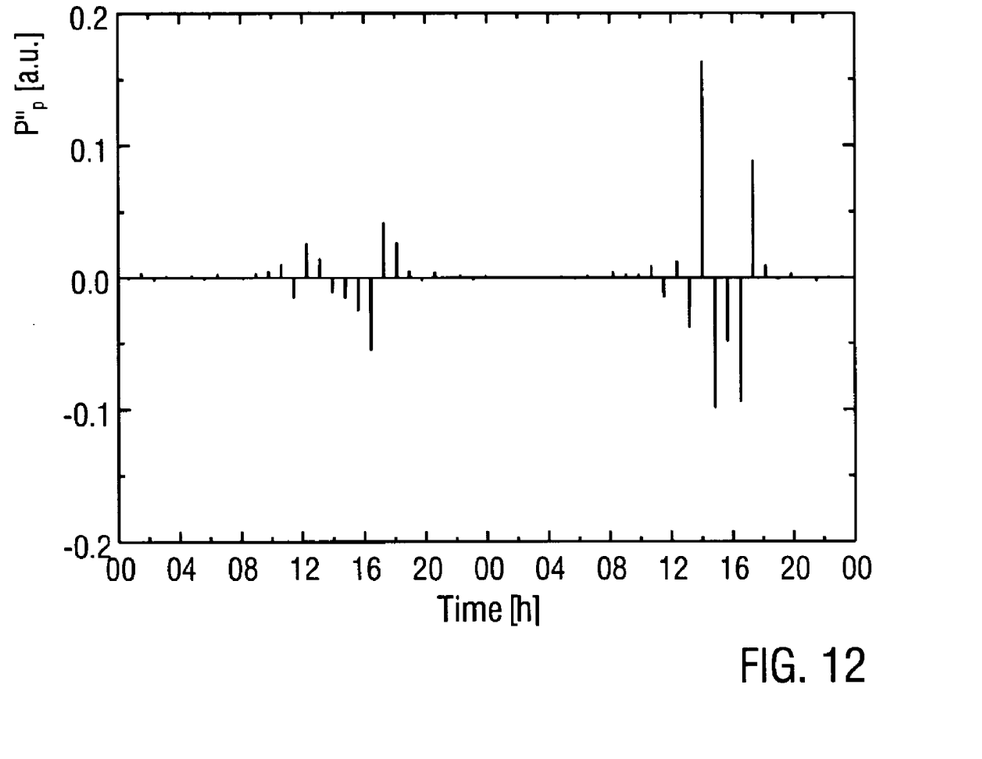

FIGS. 8 to 12 exemplary illustrate experimental result obtained with the inventive technique with various types of leaves. FIG. 8 shows output pressure values (y axis, arbitrary units) in dependency on time (x axis, 7 days) measured on a grapevine leaf. The $P_p$ values have been subjected to an interpolation. On the basis of the interpolated data, first (FIG. 9) and second (FIG. 10) derivatives have been calculated. The first and second derivatives represent quantitative changing measures of the pressure response values, which can be used for further processing, e.g. for controlling an irrigation device. FIGS. 11 and 12 show first and second derivatives of interpolated output pressure values measured with lianas leaves. As an advantage, any drifts of the baseline signal (FIG. 8) are eliminated with the derivatives. Furthermore, the curves of first and second derivatives provide optimized patterns which can be subjected to a threshold procedure.

The experimental curve show the relationship of the pressure parameters obtained with the water status of the plants and correspondingly the capability of using them for controlling irrigation devices. Measurements on bananas, Avocado, lianas and trees have given similar results.

The first or second derivatives can be further processed as the pressure parameter to be determined. Alternatively, the measured pressure response value(s) (e.g. according to FIG. 8) or the cell turgor pressure calculated there from can be further processed as the pressure parameter to be determined.

The features of the invention disclosed in the above description, the drawings and the claims can be of significance both individually as well as in combination for the realisation of the invention in its various embodiments.

The invention claimed is:

1. Method of determining a pressure parameter of a plant sample, comprising the steps of:
   subjecting the plant sample to a clamp pressure ($p_{clamp}$) created with a clamp device, wherein the clamp pressure ($p_{clamp}$) is adjusted such that the plant sample has a viscoelastic pressure response to the clamp pressure ($p_{clamp}$),
   measuring at least one pressure response value ($p_p$) of the plant sample, which depends on the clamp pressure ($p_{clamp}$), and
   determining the pressure parameter on the basis of the at least one pressure response value ($p_p$).

2. Method according to claim 1, wherein the clamp pressure ($p_{clamp}$) clamp) is adjusted with an initial calibration of the clamp device including the steps
   subjecting the plant sample to multiple test clamp pressures pulses,
   measuring a relaxation response of the plant sample, and
   selecting a particular test clamp pressure as the clamp pressure ($p_{clamp}$) if the relaxation response for the particular test clamp pressure results in an at least partial relaxation of the plant sample.

3. Method according to claim 1, wherein the clamp pressure ($p_{clamp}$) is adjusted on the basis of predetermined reference plant data.

4. Method according to claim 1, wherein the at least one pressure response value comprises at least one of an attenuated clamp pressure of the plant sample, an output force of the plant sample and an electrical conductivity of the plant sample.

5. Method according to claim 1, wherein the pressure parameter to be determined comprises at least one of the at least one pressure response value, a cell turgor pressure ($p_c$) and a quantitative changing measure of the pressure response values.

6. Method according to claim 5, wherein the cell turgor pressure ($p_c$) is determined on the basis of at least one transfer function value ($T_f(p_{clamp}, p_p)$) depending on the clamp pressure ($p_{clamp}$) and the attenuated clamp pressure.

7. Method according to claim 6, wherein the at least one transfer function value ($T_f(p_{clamp}, P_p)$) depends on a quotient of the attenuated clamp pressure and the clamp pressure ($p_{clamp}$) with $T_f = T_f(P_p/(F_a \cdot p_{clamp}))$, with $F_a$ being an attenuation factor.

8. Method according to claim 5, wherein the step of determining the quantitative changing measure comprises determining of at least one of
   a difference quotient of subsequent pressure response values,
   a first derivative of the pressure response values,
   a second derivative of the pressure response values,
   a fluctuation rate of the pressure response values, and
   a variation pattern of the pressure response values.

9. Method according to claim 8, wherein the pressure response values are measured at at least one of a varying environmental condition of the plant sample and a varying physiological condition of the plant sample.

10. Method according to claim 9, wherein the quantitative changing measure of the pressure response values is determined with respect to said at least one of the varying environmental condition and the varying physiological condition.

11. Method according to claim 9, further comprising the step of selecting a measurement location on the plant sample with respect to a distance thereof to at least one of an edge of the plant sample and a structural element on the plant sample surface.

12. Method according to claim 9, wherein
   the varying environmental condition comprises at least one of illumination intensity, temperature, relative humidity, wind speed, and
   the varying physiological condition comprises at least one of transpiration, stomata activity, photosynthesis, an active substance concentration, a hormone concentration, a pesticide concentration and a herbicide concentration.

13. Method according to claim 1, wherein the adjusting step comprises at least one of the steps:
   selecting a clamping pad of the clamp device in dependence on a type of the plant sample, and
   selecting a clamp arm length of the clamp device in dependence on a type of the plant sample (1).

14. Method according to claim 1, further comprising at least one of the steps of
   measuring at least one of illumination intensity, temperature, relative humidity, wind speed, transpiration condition, and photosynthesis condition,
   monitoring the plant sample with a camera device, and
   injecting an active substance into the plant sample.

15. Method according to claim 14, wherein the injected active substance comprises at least one of a hormone, a pesticide and a herbicide.

16. Method according to claim 1, further comprising the step of measuring a gradient of the pressure parameter or the cell turgor pressure ($p_c$) along a plant sample surface.

17. Method according to claim 1, further comprising the step of determining a variation of the pressure parameter or the cell turgor pressure ($p_c$) in response to an injection of at least one of an active substance, a hormone, a pesticide and a herbicide.

18. Method according to claim 1, further comprising the steps of
   comparing the pressure parameter or the cell turgor pressure ($p_c$) with at least one reference value, and
   generating a control signal in dependence on a result of the comparing step.

19. Method according to claim 1, further comprising the step of sending at least one of the pressure response values, the pressure parameter, the cell turgor pressure ($p_c$) and the control signal to an operation installation or a central control device.

20. Method according to claim 19, wherein the operation installation is an irrigation device, which is controlled with the at least one of the pressure response values, the pressure parameter, the cell turgor pressure ($p_c$) and the control signal.

21. Method according to claim 1, wherein the steps of subjecting the plant sample to the clamp pressure ($p_{clamp}$) and measuring the pressure response values ($p_p$) of the plant sample are conducted on different sides of the plant sample.

22. Method according to claim 1, further comprising the step of supplying energy using a solar cell or a fuel cell device.

23. Method according to claim 22, wherein the energy is supplied in dependency on the time of day.

24. Computer program residing on a computer-readable medium, with a program code for carrying out at least one step of a method of determining a pressure parameter of a plant sample according to claim 1.

25. Apparatus comprising a computer-readable storage medium containing program instructions for carrying out at least one step a method of determining a pressure parameter of a plant sample according to claim 1.

26. Apparatus for determining a pressure parameter of a plant sample, comprising:
   a clamp device adapted for subjecting the plant sample to a clamp pressure ($p_{clamp}$), a sensor device adapted for sensing at least one pressure response value ($p_p$) of the plant sample, wherein the at least one pressure response value ($p_p$) depends on the clamp pressure ($p_{clamp}$) and
   an adjusting device, which is adapted for adjusting the clamp pressure ($p_{clamp}$), such that the plant sample has an viscoelastic pressure response to the clamp pressure ($p_{clamp}$).

27. Apparatus according to claim 26, further comprising an evaluating device, which is adapted for determining a quantitative changing measure of the pressure response values, wherein the changing measure represents the pressure parameter to be determined.

28. Apparatus according to claim 26, wherein the clamp device comprises at least one of a spring clamp device, a screw clamp device, an acoustic clamp device, a magnetic field clamp device and an electrical field clamp device.

29. Apparatus according to claim 26, wherein the sensor device includes at least one pressure sensor, at least one force sensor or at least one electrical conductivity sensor.

30. Apparatus according to claim 26, wherein the clamp device comprises at least one of
   a variable clamp arm length,
   a variable clamp area,
   at least one exchangeable clamp pad,
   at least one clamp pad with adjustable pad shape,
   at least one clamp pad with a structured pad surface,
   at least one transparent clamp pad,
   at least one porous clamp pad,
   at least one clamp pad with a matching surface coating,
   at least one clamp pad with an integrated injection device,
   at least one clamp pad with multiple sensors, a light guiding device, and
an electrode device.

31. Apparatus according to claim 26, comprising: at least one sensor adapted for sensing at least one of at least one environmental condition and at least one physiological condition of the plant sample.

32. Apparatus according to claim 31, wherein: the at least one sensor is adapted for sensing at least one of an illumination intensity, temperature, relative humidity, wind speed, a transpiration condition, a photosynthesis condition, an active substance concentration, a hormone concentration, a pesticide concentration and a herbicide concentration.

33. Apparatus according to claim 26, further comprising: a protection device for protecting against at least one of humidity, extreme temperature and mechanical impact.

34. Apparatus according to claim 26, further comprising: a data port device being adapted for data transmission.

35. Apparatus according to claim 34, wherein: the data port device is configured for a connection with at least one of a telemetric system and a data network.

36. Irrigation installation, comprising:
at least one pressure parameter determining apparatus according to claim 26, and
at least one irrigation operation device, which can be controlled in dependence on the pressure parameter determined with the at least one pressure parameter determining apparatus.

37. Irrigation installation according to claim 36, wherein a network of pressure parameter determining apparatuses is connected with the at least one irrigation operation device.

38. Irrigation installation according to claim 36, further comprising at least one of
a camera device, and
a weather monitoring station.

* * * * *